(12) United States Patent
Sachdeva

(10) Patent No.: US 7,003,472 B2
(45) Date of Patent: Feb. 21, 2006

(54) METHOD AND APPARATUS FOR AUTOMATED GENERATION OF A PATIENT TREATMENT PLAN

(75) Inventor: Rohit C. L. Sachdeva, Plano, TX (US)

(73) Assignee: OraMetrix, Inc., Richardson, TX (US)

( * ) Notice: Subject to any disclaimer, the term of this patent is extended or adjusted under 35 U.S.C. 154(b) by 210 days.

(21) Appl. No.: 10/607,901

(22) Filed: Jun. 27, 2003

(65) Prior Publication Data
US 2004/0002873 A1  Jan. 1, 2004

Related U.S. Application Data

(63) Continuation-in-part of application No. 09/452,033, filed on Nov. 30, 1999, now Pat. No. 6,587,828.

(51) Int. Cl.
*G06F 17/60* (2006.01)
(52) U.S. Cl. .......................................................... 705/1
(58) Field of Classification Search ...................... 705/1
See application file for complete search history.

(56) References Cited

U.S. PATENT DOCUMENTS

| | | | |
|---|---|---|---|
| 5,011,405 A | 4/1991 | Lemchen | 433/24 |
| 5,338,198 A | 8/1994 | Wu et al. | 433/213 |
| 5,395,238 A | 3/1995 | Andreiko et al. | 433/24 |
| 5,518,397 A | 5/1996 | Andreiko et al. | 433/24 |
| 5,533,895 A | 7/1996 | Andreiko et al. | 433/24 |
| 5,618,176 A | 4/1997 | Andreiko et al. | 433/11 |
| 5,826,237 A * | 10/1998 | Macrae et al. | 705/2 |
| 5,879,158 A | 3/1999 | Doyle | 433/24 |
| 5,975,893 A | 11/1999 | Chishti et al. | 433/6 |
| 6,014,629 A * | 1/2000 | DeBruin-Ashton | 705/2 |

(Continued)

FOREIGN PATENT DOCUMENTS

WO    WO 9901832 A1 *  1/1999

OTHER PUBLICATIONS

Bisby, Adam, "Health care market goes the distance." Computer Dealer News, Aug. 10, 1998.*

*Primary Examiner*—John Weiss
*Assistant Examiner*—Jonathan Ouellette
(74) *Attorney, Agent, or Firm*—McDonnell Boehnen Hulbert & Berghoff LLP

(57) ABSTRACT

A method and apparatus for generating a patient treatment plan includes processing that begins by providing a list of health care services to a patient and/or care provider. The processing continues by prompting for input of digital information regarding the patient when health care services applicable to addressing the patient's treatment needs have been concurrently selected. The processing continues by determining whether a sufficient amount of digital information has been received. If so, the processing continues by simulating treatment of a patient based on the digital information, a treatment objective, and normalized patient data. The processing then continues by generating the patient treatment plan in accordance with the simulating of the treatment when the simulated treatment results have been acknowledged.

18 Claims, 6 Drawing Sheets

U.S. PATENT DOCUMENTS

| | | |
|---|---|---|
| 6,015,289 A | 1/2000 | Andreiko et al. ............... 433/3 |
| 6,068,482 A | 5/2000 | Snow .......................... 433/223 |
| 6,099,314 A | 8/2000 | Kopelman et al. .......... 433/213 |
| 6,227,850 B1 | 5/2001 | Chishti et al. ................. 433/24 |
| 6,236,878 B1 * | 5/2001 | Taylor et al. ................ 600/416 |
| 6,315,553 B1 | 11/2001 | Sachdeva et al. ............. 433/24 |
| 6,350,120 B1 | 2/2002 | Sachdeva et al. ............. 433/24 |
| 6,464,496 B1 | 10/2002 | Sachdeva et al. ............. 433/24 |
| 6,471,512 B1 | 10/2002 | Sachdeva et al. ............. 433/24 |
| 6,512,994 B1 | 1/2003 | Sachdeva ...................... 433/24 |
| 6,540,512 B1 | 4/2003 | Sachdeva et al. ............. 433/24 |
| 6,587,828 B1 * | 7/2003 | Sachdeva ........................ 705/1 |

* cited by examiner

METHOD AND APPARATUS FOR AUTOMATED GENERATION OF A PATIENT TREATMENT PLAN

CROSS-REFERENCE TO RELATED APPLICATION

This is a continuation-in-part of application Ser. No. 09/452,033 filed Nov. 30, 1999, now issued as U.S. Pat No. 6,587,828.

TECHNICAL FIELD OF THE INVENTION

This invention relates generally to the practice of orthodontics and in particular to a method and apparatus for treating an orthodontic patient.

BACKGROUND OF THE INVENTION

Orthodontics is the practice of manipulating a patient's teeth to provide better function and appearance. In general, brackets are bonded to a patient's teeth and coupled together with an arch wire. The combination of the brackets and wire provide a force on the teeth causing them to move. Once the teeth have moved to a desired location and are held in a place for a certain period of time, the body adapts bone and tissue to maintain the teeth in the desired location. To further assist in retaining the teeth in the desired location, a patient may be fitted with a retainer.

To achieve tooth movement, orthodontists utilize their expertise to first determine a three-dimensional mental image of the patient's physical orthodontic structure and a three-dimensional mental image of a desired physical orthodontic structure for the patient, which may be assisted through the use of x-rays and/or models. Based on these mental images, the orthodontist further relies on his/her expertise to place the brackets and/or bands on the teeth and to manually bend (i.e., shape) wire, such that a force is asserted on the teeth to reposition the teeth into the desired physical orthodontic structure. As the teeth move towards the desired location, the orthodontist makes continual judgments as to the progress of the treatment, the next step in the treatment (e.g., new bend in the wire, reposition or replace brackets, is head gear required, etc.), and the success of the previous step.

In general, the orthodontist makes manual adjustments to the wire and/or replaces or repositions brackets based on his or her expert opinion. Unfortunately, in the oral environment, it is impossible for a human being to accurately develop a visual three-dimensional image of an orthodontic structure due to the limitations of human sight and the physical structure of a human mouth. In addition, it is humanly impossible to accurately estimate three-dimensional wire bends (with an accuracy within a few degrees) and to manually apply such bends to a wire. Further, it is humanly impossible to determine an ideal bracket location to achieve the desired orthodontic structure based on the mental images. It is also extremely difficult to manually place brackets in what is estimated to be the ideal location. Accordingly, orthodontic treatment is an iterative process requiring multiple wire changes, with the process success and speed being very much dependent on the orthodontist's motor skills and diagnostic expertise. As a result of multiple wire changes, patient discomfort is increased as well as the cost. As one would expect, the quality of care varies greatly from orthodontist to orthodontist as does the time to treat a patient.

As described, the practice of orthodontic is very much an art, relying on the expert opinions and judgments of the orthodontist. In an effort to shift the practice of orthodontic from an art to a science, many innovations have been developed. For example, U.S. Pat. No. 5,518,397 issued to Andreiko, et. al. provides a method of forming an orthodontic brace. Such a method includes obtaining a model of the teeth of a patient's mouth and a prescription of desired positioning of such teeth. The contour of the teeth of the patient's mouth is determined, from the model. Calculations of the contour and the desired positioning of the patient's teeth are then made to determine the geometry (e.g., grooves or slots) to be provided. Custom brackets including a special geometry are then created for receiving an arch wire to form an orthodontic brace system. Such geometry is intended to provide for the disposition of the arched wire on the bracket in a progressive curvature in a horizontal plane and a substantially linear configuration in a vertical plane. The geometry of the brackets is altered, (e.g., by cutting grooves into the brackets at individual positions and angles and with particular depth) in accordance with such calculations of the bracket geometry. In such a system, the brackets are customized to provide three-dimensional movement of the teeth, once the wire, which has a two dimensional shape (i.e., linear shape in the vertical plane and curvature in the horizontal plane), is applied to the brackets.

Other innovations relating to bracket and bracket placements have also been patented. For example, such patent innovations are disclosed in U.S. Pat. No. 5,618,716 entitled "Orthodontic Bracket and Ligature" a method of ligating arch wires to brackets, U.S. Pat. No. 5,011,405 "Entitled Method for Determining Orthodontic Bracket Placement," U.S. Pat. No. 5,395,238 entitled "Method of Forming Orthodontic Brace," and U.S. Pat. No. 5,533,895 entitled "Orthodontic Appliance and Group Standardize Brackets therefore and methods of making, assembling and using appliance to straighten teeth".

Unfortunately, the current innovations to change the practice of orthodontic from an art to a science have only made limited progress. This limit is due to, but not restricted to, the brackets being the focal point for orthodontic manipulation. By having the brackets as the focal point, placement of each bracket on a corresponding tooth is critical. Since each bracket includes a custom sized and positioned wire retaining groove, a misplacement of a bracket by a small amount (e.g., an error vector having a magnitude of millimeter or less and an angle of a few degrees or less) can cause a different force system (i.e., magnitude of movement and direction of movement) than the desired force system to be applied to the tooth. As such, the tooth will not be repositioned to the desired location.

Another issue with the brackets being the focal point is that once the brackets are placed on the teeth, they are generally fixed for the entire treatment. As such, if the treatment is not progressing as originally calculated, the orthodontist uses his or her expertise to make the appropriate changes. The treatment may not progress as originally calculated for several reasons. For example, misplacement of a bracket, misapplication of a bend in the wire, loss or attrition of a bracket, bonding failure, the patient falls outside of the "normal" patient model (e.g., poor growth, anatomical constraints, etc.), patient lack of cooperation in use of auxiliary appliance, etc. are factors in delayed treatment results. When one of these conditions arise, the orthodontist utilizes his or her expertise to apply manual bends to the wire to "correct" the errors in treatment. Thus, after the original scientific design of the brackets, the practice of the orthodontic converts back to an art for many patients for the remainder of the treatment.

Another issue with the brackets being the focal point is that customized brackets are expensive. A customized bracket is produced by milling a piece of metal (e.g., stainless steel, aluminum, ceramic, titanium, etc.) and tumble polishing the milled bracket. While the milling process is very accurate, some of the accuracy is lost by tumble polishing. Further accuracy is lost in that the placement of the brackets on the teeth and installation of the wire are imprecise operations. As is known, a slight misplacement of one bracket changes the force on multiple teeth and hinders treatment. To assist in the placement of the custom brackets, they are usually shipped to the orthodontist in an installation jig. Such an installation jig is also expensive. Thus, such scientific orthodontic treatment is expensive and has many inherent inaccuracies.

Therefore, a need exists for a method and apparatus that provides a scientific approach to orthodontics throughout the treatment of a patient, maintains treatment costs, and provides a more consistent treatment time, especially with respect to automation of treatment plan generation.

SUMMARY

Generally, the present invention provides a method and computer apparatus for generating a patient treatment plan. Such a method and apparatus includes processing that begins by providing a list of health care services to a patient and/or care provider. In one embodiment of the invention, the processing continues by prompting the user to input interactively a selection of a plurality of health care services from the list of health care services. Multiple health care services (e.g, orthodontic, dental, surgical and/or medical) can be selected essentially concurrently or simultaneously, one after the other, as the user operates with the apparatus to select the services that are desired for use in treatment of the patient. The user is prompted to enter or input digital information regarding the patient when a health care service has been selected. Such information could be for example patient diagnosis information, image information (X-ray, scan, or other type of information). The processing continues by determining a treatment objective for the patient, which may be automated or with some user involvement. Then the processing continues by simulating treatment of a patient based on the digital information, a treatment objective, the selected health care services, and normalized patient data. The processing results in a simulated treatment result. The processing then continues by generating the patient treatment plan in accordance with the simulating of the treatment when the simulated treatment results have been acknowledged. With such a method and apparatus, the generation of a patient treatment plan may be automated for particular types of health care services, including orthodontic care, dental care, cosmetic care including orthognathic, craniofacial, oral or plastic surgery, and medical care.

In one possible embodiment, the invention is practiced as a series of software instruction which are executable on a workstation the incorporates a general purpose computer. The workstation can be installed at the site of treatment of the patient, such as in an orthodontic or dental clinic.

DETAILED DESCRIPTION OF A PREFERRED EMBODIMENT

Figure 1:
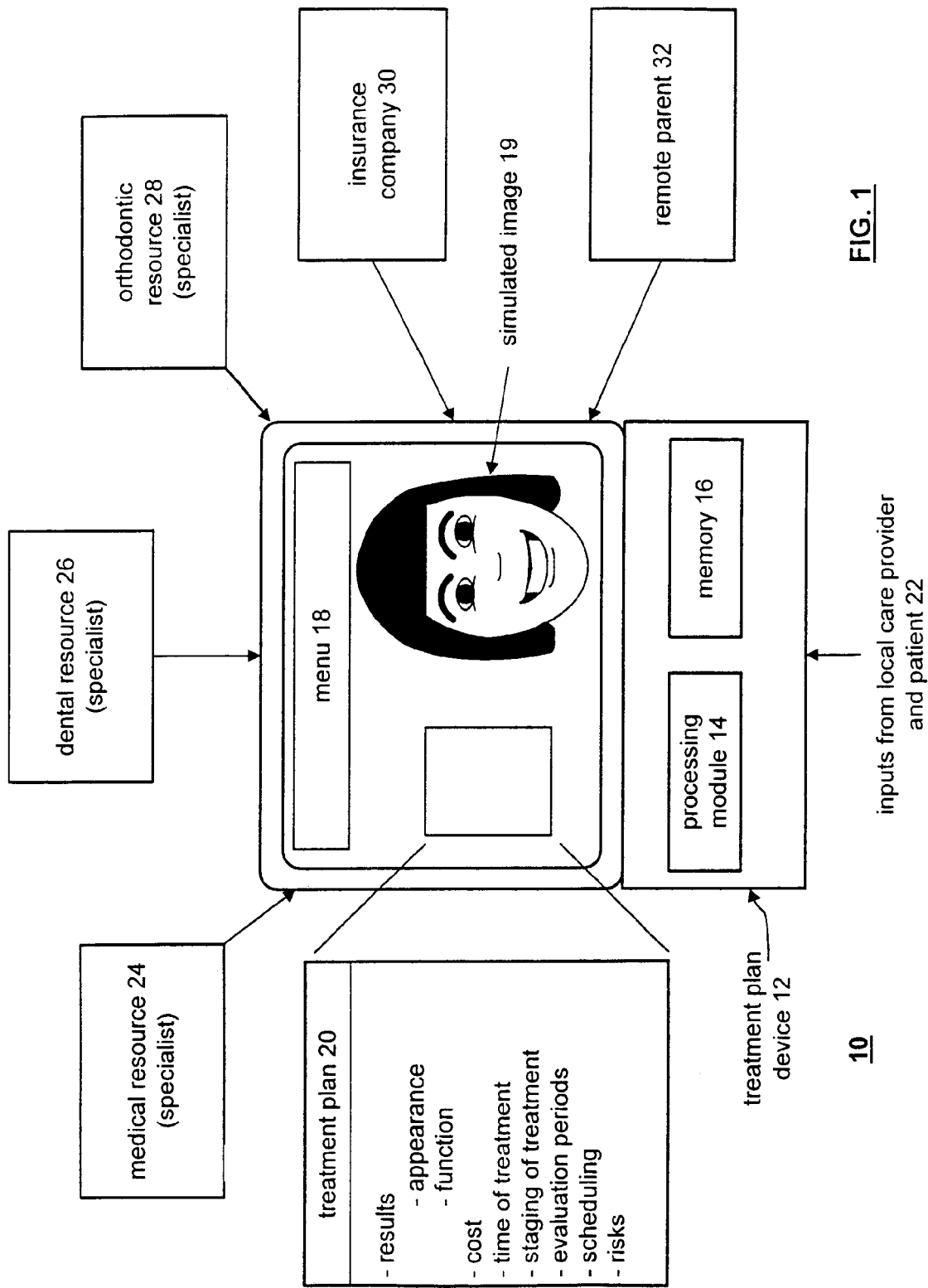
FIG. 1 illustrates a graphical diagram of a treatment plan device in accordance with the present invention.

The present invention can be more fully described with reference to FIGS. 1 through 5. FIG. 1 illustrates a graphical diagram of an orthodontic treatment system 10 that includes a treatment plan device 12. The treatment plan device 12 includes a processing module 14 and memory 16. The processing module 14 may be a single processing device or a plurality of processing devices. Such a processing device may be a microcontroller, microcomputer, microprocessor, central processing unit, a digital signal processor, state machine, logic circuitry, and/or any device that manipulates signals (e.g., analog and/or digital) based on operational instructions. The memory 16 may be a single memory device or a plurality of memory devices. Such a memory device may be a read-only memory, random access memory, floppy disk memory, flash memory, and/or any device that stores operational instructions. Note that when the processing module implements one or more functions via a state machine and/or logic circuitry, the memory storing the corresponding operational instructions is embedded within the circuitry comprising the state machine and/or logic circuitry.

The treatment plan device 12 is operably coupled to receive inputs from a local care provider and/or a patient 22. Such inputs include the digital information required to generate a treatment plan. The digital information may include one or more of: the patient's chief complaint, the patient's medical history, the patient's dental history, clinical examination, three-dimensional images of the patient's orthodontic structure, video graphic examination, functional examination information, soft tissue evaluation, skeletal evaluation, and patient's objectives. In addition, the digital information may include cost constraints based on the patient's insurance carrier and/or financial status. Further, the digital information includes the length of treatment the patient is willing to undergo, the patient's commitment level to adhering to treatment, etc.

The treatment plan device 12 includes firmware to display a menu 18 and a treatment plan 20. The treatment plan device 12 may further include firmware to display a simulated image 19, or exterior appearance model. The menu 18 may include the list of health care services such as dental services, orthodontic services, cosmetic services and/or medical services, a list of orthodontic or dental products (e.g., tooth paste, floss, etc.), and/or resources of orthodontic information (e.g., factual information, care, etc.). The patient and/or care provider selects from one of these health care categories and is subsequently provided with a menu that offers selection of one of well-care, health care, and/or follow-up care. Note that the health care category may further be divided into acute or chronic ailments where a series of prompts are provided in accordance with such information. For example, if a patient has selected health care and the situation is acute, the treatment plan device 12 may automatically call 911. Alternately, all health care services applicable to addressing the patient's treatment needs can be selected concurrently and interactively. As such, via the treatment plan device 12, the patient with or without the assistance of a local care provider can initiate the generation of a treatment plan for him or herself. Further note that the well-care category provides a list of options for well-care treatment. For example, the well-care category for orthodontic patients may include information on re-installing an arch wire, list of foods that should be avoided, brushing and flossing advise, etc.

To facilitate the generation of the treatment plan 20, the treatment plan device 12 may interface with a medical resource 24, a dental resource 26, an orthodontic resource 28, an insurance company 30, other resources (not shown), and/or a remote parent 32. Based on input from one or more of these sources and the inputs provided by the patient and/or local care provider, the treatment plan device 12 generates the treatment plan 20. The treatment plan will include results, which may be based on appearance and/or function, costs of treatment, time for treatment, staging of treatment events, evaluation periods, scheduling, and associated risks. Note that the scheduling may be done via the Internet or other mechanism. Further note that the medical resource 24, the dental resource 26, and the orthodontic resource 28 may be local to the treatment plan device, (i.e., coupled via a local area network), or may be remotely coupled through a wide area network and/or the Internet. Further note that the treatment plan device may be included in a site orthodontic system and/or an orthodontic server as described in patent application Ser. No. 09/451,637, now U.S. Pat. No. 6,471,562, entitled METHOD AND APPARATUS FOR DETERMINING AND MONITORING ORTHODONTIC TREATMENT, in patent application Ser. No. 09/451,560, now U.S. Pat. No. 6,540,512, entitled METHOD AND APPARATUS FOR TREATING AN ORTHODONTIC PATIENT, and in a patent application Ser. No. 09/452,038, now U.S. Pat. No. 6,315,553, entitled METHOD AND APPARATUS FOR SITE TREATMENT OF AN ORTHODONTIC PATIENT. Each of these patent applications has a filing date of Nov. 30, 1999 and is assigned to the same assignee as the present invention. The contents of these patents are incorporated by reference herein.

Figure 2:
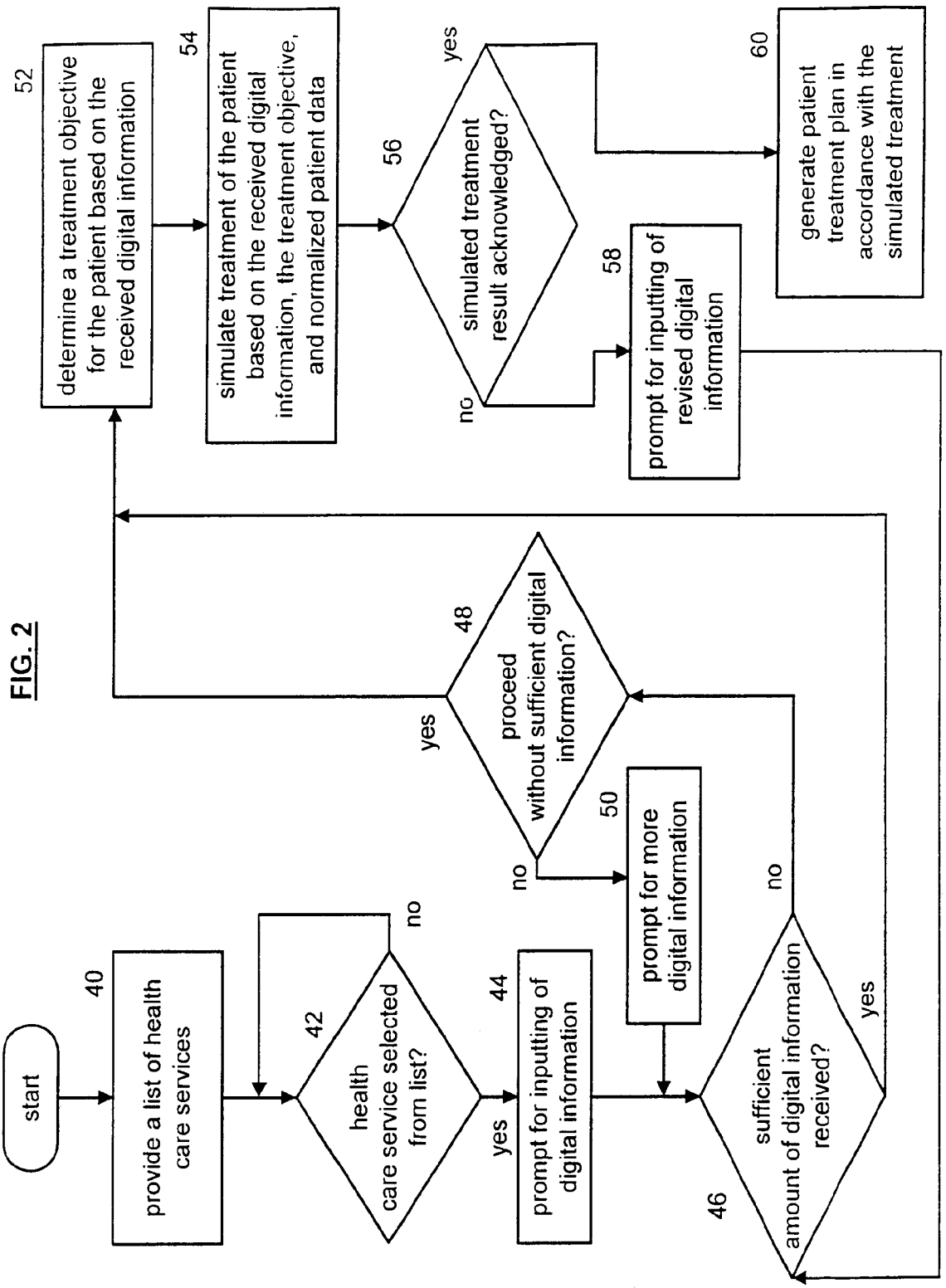
FIG. 2 illustrates a logic diagram of a method for generating a patient treatment plan in accordance with one embodiment of the invention.

FIG. 2 illustrates a logic diagram of a method for generating a patient treatment plan for a patient who is just beginning treatment or has received some treatment. The steps of FIG. 2 may be implemented as operational instructions and executed by processing module 14 and stored in memory 16 of the treatment plan device 12. The process begins at step 40 where a list of health care services is provided. The list of health care services is provided on screen to a patient and/or local care provider. The display provided may be a graphical user interface that includes graphics, text, voice inputs, or a combination thereof that allow the patient and/or local service care provider to select one or more of the health care services. The list of health care services may include orthodontic services, dental services, cosmetic services including orthognathic, craniofacial, oral or plastic surgery services, and/or medical services, which may be inter disciplinary or multi-disciplinary. Each of these service categories may include subcategories as well. For example, the subcategories may include well-care treatment, emergency treatment, chronic treatment, and/or follow-up treatment in a limited or comprehensive manner. In a preferred embodiment, the user is prompted to select a plurality of health care services for treatment of the patient. For example, the user is prompted to select orthodontic services, and cosmetic surgery services.

The process then proceeds to step 42 where a determination is made as to whether a health care service has been selected from the list. Once the health care service or services have been selected, the process proceeds to step 44 where a prompt is provided that requests the user (i.e., the patient and/or local health care provider) to input digital information regarding the patient. Although not shown in FIG. 2, at step 42, in one possible embodiment, all health care services applicable to addressing the patient's treatment needs are selected simultaneously and interactively, and the process proceeds by providing digital information regarding the patient. For example, the digital information of an orthodontic patient includes a digital model of the patient's malocclusion, patient's chief compliant, patient's demands, financial constraints, treatment length, desired orthodontic function, desired orthodontic appearance, the patient's dental history, the patient's medical history, and/or acceptable deviations. In addition, the digital information may include normalized patient data that includes orthodontic parameters relating to the patient. The normalized patient data may be retrieved from a database of orthodontic parameters as described in U.S. Pat. No. 6,315,553.

The process then proceeds to step 46 where a determination is made as to whether a sufficient amount of data has been received. Of the digital information previously described, some information is essential for determining a treatment plan while other pieces of data are peripheral to treatment. For example, a digital model of the patient's malocclusion, the patient's personal information (e.g., age, sex, race, etc.) and the desired orthodontic results are essential. Other information such as treatment length, financial constraints, the patient's dental history, the patient's medical history, and acceptable deviations may be peripheral information. As such, at step 46 a determination is made as to whether the essential information has been received.

If a sufficient amount of data has not been received, the process proceeds to step 48 where a determination is made as to whether the process is to proceed without the sufficient digital information. If not, the process proceeds to step 50 where a prompt is provided requesting more digital information. Note that, at step 48, the patient and/or local service care provider may request that the process proceed without further digital information.

When a sufficient amount of digital information has been received, or it has been determined that the process will proceed without sufficient digital information, the process proceeds to step 52. At step 52, a treatment objective is determined for the patient based on the received digital information. The treatment objective may be arrived at with some user interaction and exercise of clinical judgment. The treatment objective may include one or more of dental appearance, orthodontic function, facial appearance, skeletal appearance and/or function, treatment time, patient's commitment to treatment, costs, etc. The process then proceeds to step 54 where treatment of the patient is simulated based on the received digital information, the treatment objective, and normalized patient data. For a more detailed discussion of the simulation of treatment refer to U.S. Pat. No. 6,431,870 entitled METHOD AND APPARATUS FOR GENERATING A DESIRED THREE-DIMENSIONAL IMAGE OF AN IDEAL ORTHODONTIC STRUCTURE, assigned to the same assignee as the present invention. The contents of the '870 patent is incorporated by reference herein.

The process then proceeds to step 56 where a determination is made as to whether the patient and/or local care provider has acknowledged the simulated treatment results. In other words, a check is made as to whether the patient and/or local care provider has approved of the simulated treatment results. If not, the process proceeds to step 58 where a prompt requests further digital information and/or requests the user to revise the digital information already provided. The process then reverts to step 46.

If the simulated treatment results have been acknowledged, the process proceeds to step 60. At step 60, the patient treatment plan is generated in accordance with the simulated treatment. The treatment plan will include precise steps for treating the patient from the patient's initial condition to the desired results. Accordingly, for an orthodontic patient, the treatment plan will include the time of treatment, a series of wires to support the treatment, bracket placement, patient care requirements, scheduling of patient visits and/or adjustments, monitoring progress to provide feedback for adjusting the treatment plan when necessary. In addition, the treatment plan may identity patient resources (e.g., chat groups, patient care web page, etc.) that assist the patient in becoming a more informed consumer. Note that the patient and/or the local care provider may change the treatment object at any time during treatment, which would cause a new treatment plan to be generated.

Figure 3:
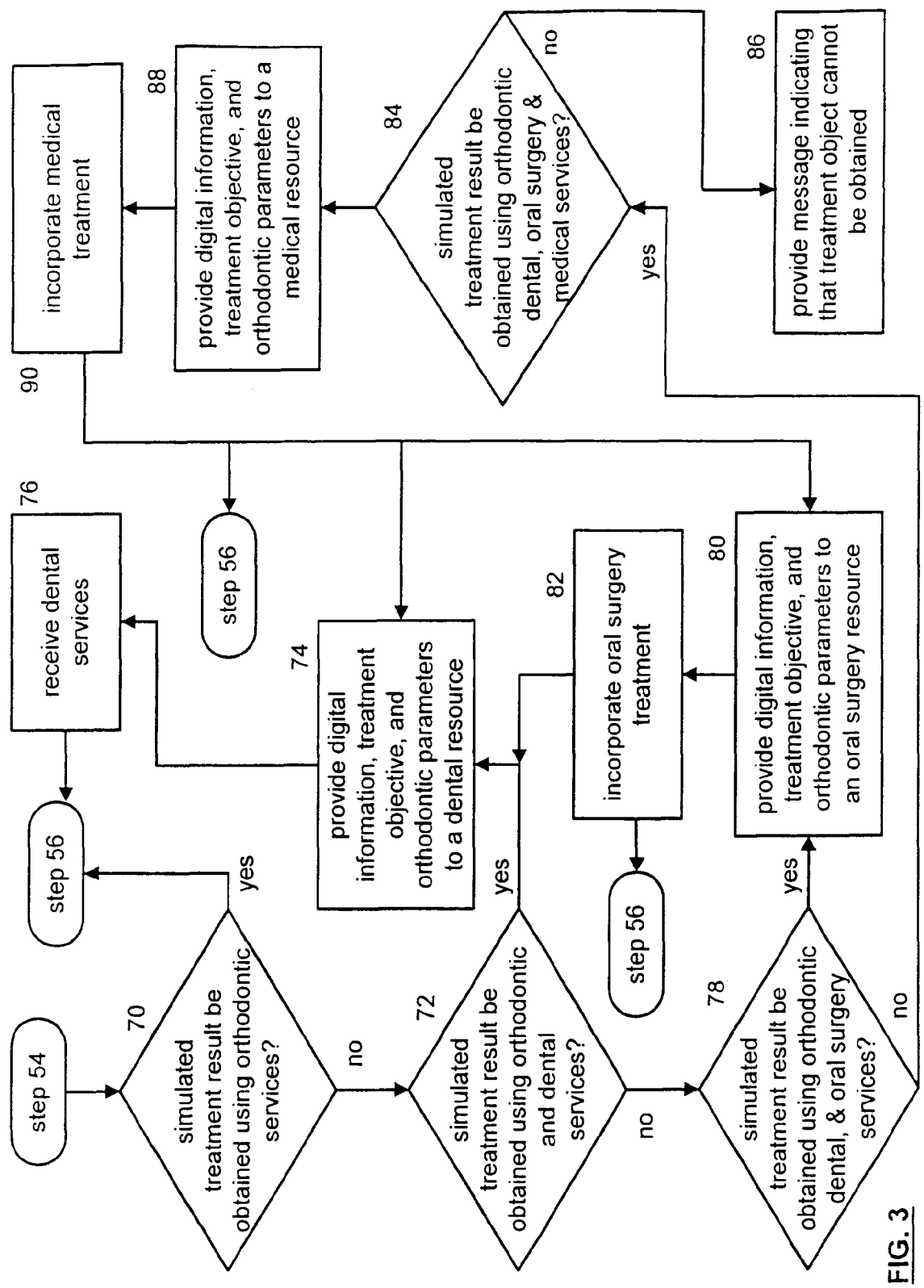
FIG. 3 illustrates a logic diagram of a method for step 54 of FIG. 2 according to one embodiment of the invention.

FIG. 3 illustrates a logic diagram of step 54 of FIG. 2 in accordance with one embodiment of the invention. The process begins at step 70 where a determination is made as to whether the simulated treatment result can be obtained using orthodontic services, i.e., does the patient only require orthodontic treatment to obtain the desired orthodontic structure. If so, the process reverts to step 56. If not, the process proceeds to step 72 where a determination is made as to whether the simulated treatment result can be obtained using orthodontic services and dental services (e.g., the patient requires at least one tooth to be extracted prior to orthodontic treatment). If so, the process proceeds to step 74 where digital information, treatment objectives, and orthodontic parameters are provided to a dental resource. The process then proceeds to step 76 where inputs from the dental services are received (e.g., which tooth to extract, how the extraction should be done, recovery time, etc). The process then proceeds to step 56 where the treatment plan is generated in accordance with the orthodontic services and the dental services.

If at step 72, the simulated treatment result cannot be obtained using orthodontic and dental services, the process proceeds to step 78. At step 78 a determination is made as to whether a simulated treatment result can be obtained using two or more of orthodontic services, dental services, and oral surgery services (e.g., jaw extension surgery, upper arch plate separating surgery, etc.). If so, the process proceeds to step 80 where digital information, the treatment objective, and orthodontic parameters are provided to an oral surgery resource. The process then proceeds to step 82 where the oral surgery treatment is incorporated into the treatment plan. The process may then revert to steps 56 of FIG. 2 or proceed to step 74. With this option, the orthodontic services may be combined with one or more of the dental services and oral surgery services. For example, for an orthodontic patient that requires tooth extraction where at least one of the teeth is a non-erupted molar, the dental services are incorporated to extract the erupted teeth and oral surgery to remove the non-erupted molar. Further, oral surgery may be required to lengthen and/or widen the upper and/or lower jaw to provide more room for the teeth, improve the patient's physical appearance, etc.

If at step 78, the treatment plan cannot be simulated using two or more of orthodontic services, dental services, and oral surgery services, the process proceeds to step 84. At step 84, a determination is made as to whether the simulated treatment result may be obtained using one or more of orthodontic services, dental services, oral surgery services, and medical services (e.g., cosmetic surgery, medication required for the patient, etc.). Note that a patient with a pre-existing medical condition may require medication before-each orthodontic treatment. If the result at step 84 was negative, the process proceeds to step 86 where a message is provided indicating that the treatment objective cannot be obtained. At this point, the user may change one or more aspects of the digital information, change the treatment objective, and/or request that the treatment be simulated with compromised results, i.e., less than optimal results.

If, however, treatment can be obtained using two or more of the orthodontic, dental, oral surgery, and/or medical services, the process proceeds to step 88. At step 88, the digital information, the treatment plan objective, and orthodontic parameters are provided to a medical resource. The process then proceeds to step 90 where the medical resources provides a medical treatment information to the treatment plan device 12, which incorporates the medical treatment into the simulated treatment plan. The process then can proceed to step 56, 80, or 74. In this manner, a patient may be treated based on orthodontic services only, or a combination of orthodontic services, dental services, oral surgery services, and medical services. For example, a patient may require medication prior to each orthodontic visit to prevent further ailments, thus the treatment plan only embodies orthodontic services and medical services. As another example, a patient may require may require tooth extraction, via dental services, oral surgery to provide a widening of the jaw, and medical treatment for medication during the orthodontic visits and general dentistry visits.

Figure 3A:
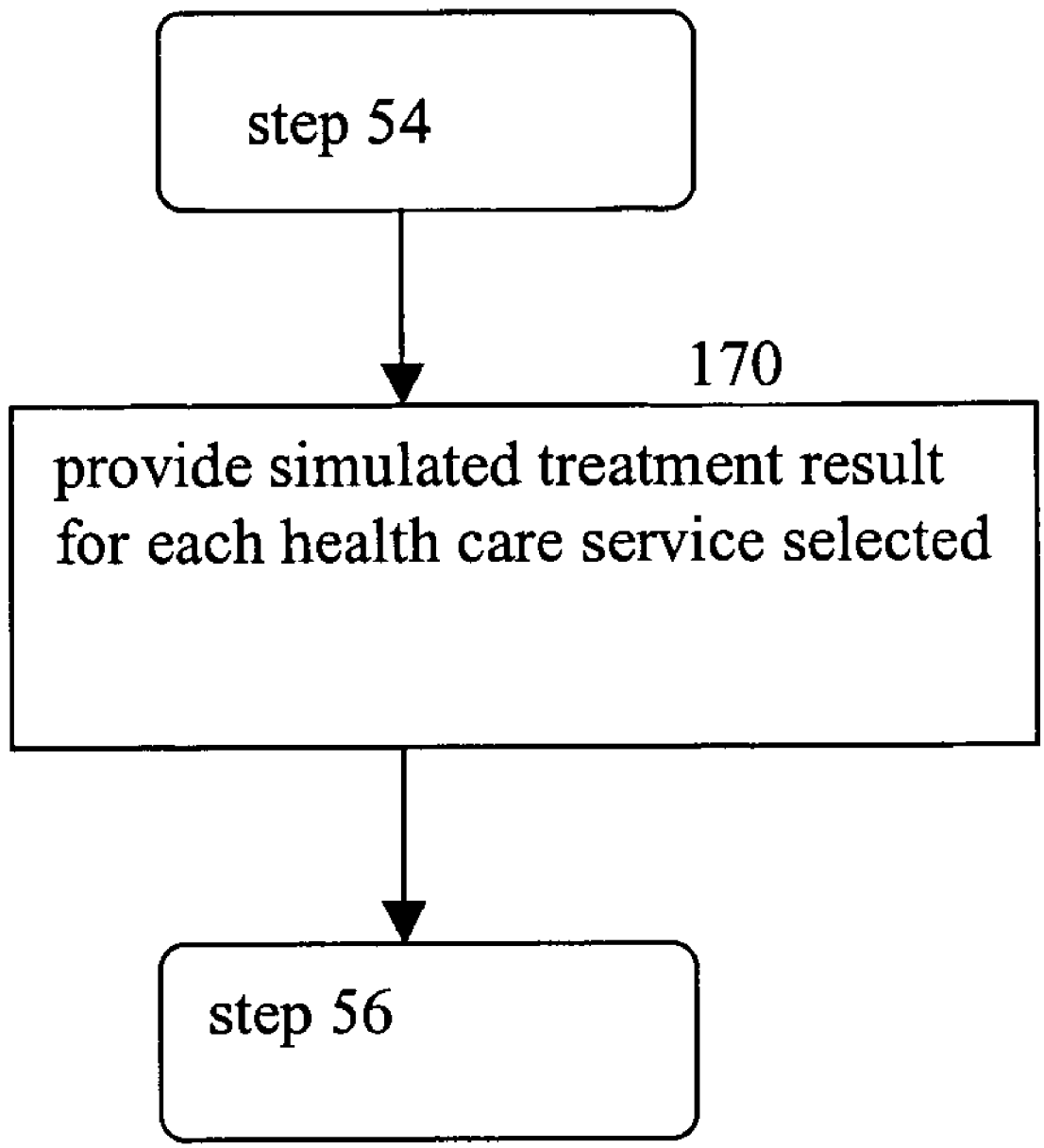
FIG. 3A illustrates a logic diagram of a method for step 54 of FIG. 2 according to another embodiment of the invention.

FIG. 3A illustrates a logic diagram of step 54 of FIG. 2 according to another embodiment of the invention. A determination is made at step 170 as to the health care services selected to address the treatment needs of the patient. The health care service categories are orthodontic, dental, cosmetic including orthognathic, craniofacial, oral, or plastic surgery, and medical. For each health care service selected a treatment plan is simulated for the patient and included in the overall treatment plan for the patient. The process then reverts to step 56.

Figure 4:
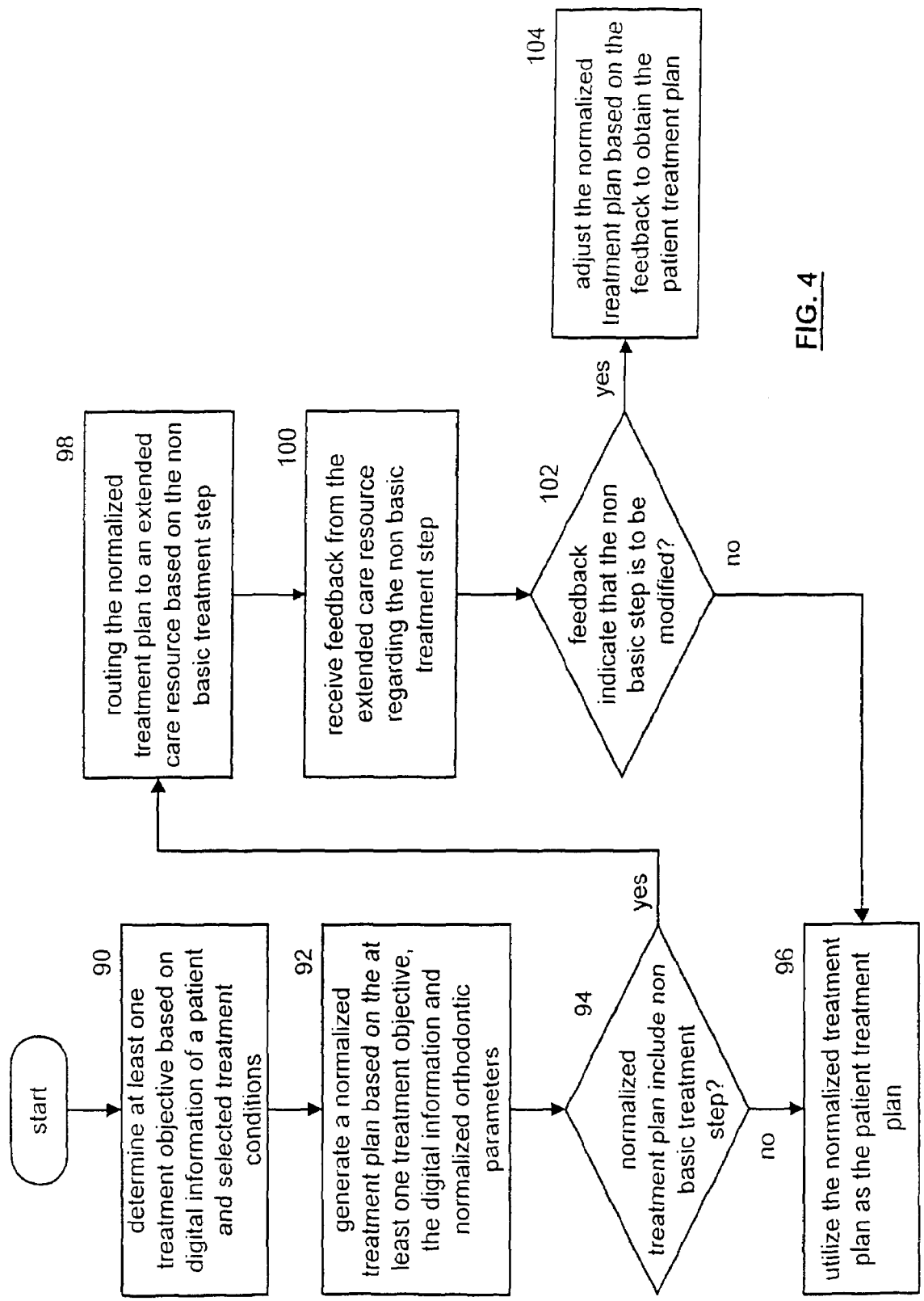
FIG. 4 illustrates a logic diagram of an alternate method for generating a patient treatment plan in accordance with the present invention.

FIG. 4 illustrates a logic diagram of an alternate method for generating a patient treatment plan. The steps of FIG. 4 may be implemented as of operational instructions that are stored in memory 16 and executed by processing module 14. Note that for processing module 14 and memory 16, they may be included in a single device or within a plurality of devices distributed throughout an orthodontic service network. For a more detailed discussion of an orthodontic service network refer to the U.S. Pat. Nos. 6,471,562, 6,540,512 and 6,315,553, which were referenced previously.

The process begins at step 90 where at least one treatment objective is determined based on digital information of a patient and selected treatment conditions. Note that the treatment objective may be determined from the information received, or it may be received as an input. The selected treatment conditions may be a subset of the digital information such as costs, treatment plan, treatment time, etc. The process then proceeds to step 92 where a normalized treatment plan is generated based on at least one of the treatment objectives, the digital information and normalized orthodontic parameters. The normalized orthodontic parameters correspond to a database of information that has been obtained from patients of similar age, sex, medical conditions, and dental conditions, etc. For a more detailed discussion of orthodontic parameters refer to the above-cited US Patents.

The process then proceeds to step 94 where a determination is made as to whether the normalized treatment plan includes a non-basic treatment step. Note that in this method, the treatment plan is generated to optimize the patient's care and may include the suggested extraction of teeth, oral surgery, bleaching of teeth, restorative needs, periodontal surgery, and/or medical procedures. To make such a determination, therapeutic decisions regarding soft tissue modification, skeletal modification, extraction, expansion, tip back, distal molar movement, interproximal reduction, flaring, axial inclination change are factors in determining the normalized treatment plan. If the normalized treatment plan does not include a non-basic step i.e., it includes only orthodontic treatment, the process proceeds to step 96 where the normalized treatment plan is utilized as the patient treatment plan.

If, however, the normalized treatment-plan includes one or more of dental services, oral surgery services, and/or medical services, the process proceeds to step 98. At step 98, the normalized treatment plan is routed to an extended care resource based on the particular non-basic treatment step. As such, the normalized treatment plan is routed to a dental resource when the normalized treatment plan includes dental services, to an oral surgery resource, when the plan includes oral surgery services, and to a medical resource, when the plan includes medical services. The process then proceeds to step 100 where feedback is received from the extended care resource regarding the non-basic treatment step. As such, the feedback regarding the step indicates whether the normalized treatment plan has accurately interpreted the corresponding non-basic treatment. Accordingly, the extended care resource is affirming or rejecting the normalized generation of the non-basic treatment step.

The process proceeds to step 102 where a determination is made as to whether the feedback indicates that the non-basic step is to be modified. If not, the process reverts to step 96. If the non-basic step is to be modified, the process proceeds to step 104 where the normalized treatment plan is adjusted based on the feedback. Having adjusted the normalized treatment plan, the patient treatment plan is obtained.

Figure 5:
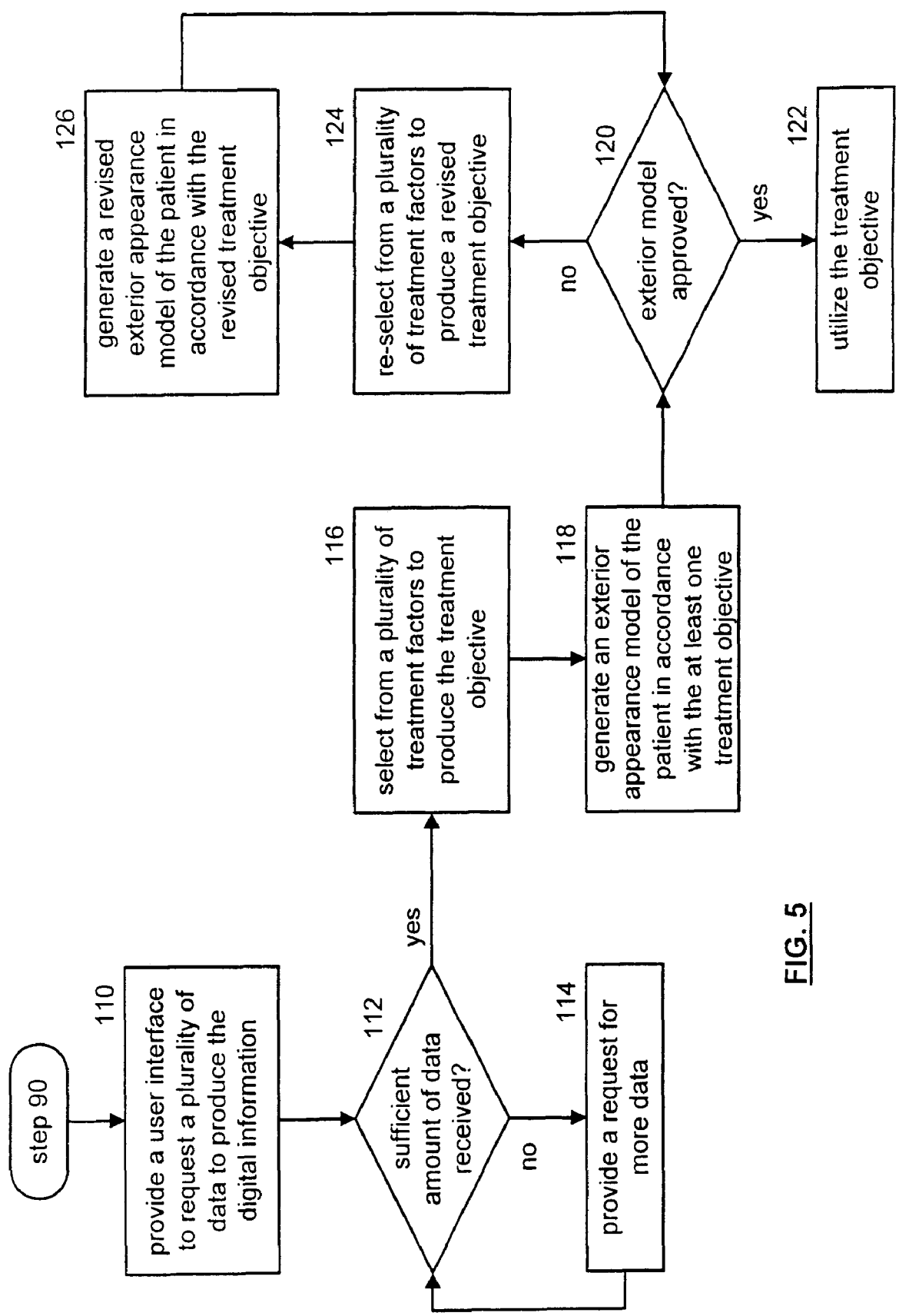
FIG. 5 illustrates a logic diagram of a method of step 90 of FIG. 4.

FIG. 5 illustrates a logic diagram for executing step 90 of FIG. 4. The process begins at step 110 where a user interface is provided to request a plurality of data, which constitutes the digital information. The process proceeds to step 112 where a determination is made as to whether a sufficient amount of data has been received. If not, the process proceeds to step 114 where a request for additional information is provided.

Once a sufficient amount of data has been received, the process proceeds to step 116. At step 116, the treatment objective is selected based on a plurality of treatment factors. Such treatment factors include patient's chief complaint, risk factors, medical and dental history, examination information, x-rays, functional examination, growth, positioning of the maxilla, positioning of the mandible, positioning of the occlusal plane, positioning of the lower incisor, positioning of the upper incisor, the lower arch form, the upper arch form, the mid-lines, arch length deficiencies, position of the upper molar, position of the lower molar, intra-arch relationships, inter-arch relationships, functional relationships, soft tissue position, care needs of the patient, and/or aesthetic relationships.

The process then proceeds to step 118 where an exterior appearance model of the patient is generated in accordance with the at least one treatment objective. The process then proceeds to step 120 where a determination is made as to whether the exterior model has been approved. If so, the process proceeds to step 122 where the treatment objective is utilized to generate the treatment plan. If not, the process proceeds to step 124 where reselection of treatment factors from a plurality of treatment factors is done to produce a revised treatment objective. The process then proceeds to step 126 where a revised exterior appearance is generated in accordance with the revised treatment objective.

The preceding discussion has presented a method and apparatus for automatically generating a treatment plan for a patient. By utilizing the automated process, a patient may receive more accurate and less expensive orthodontic treatment. In addition, the method and apparatus of the present invention provide a mechanism for converting the practice of orthodontics from an art to a science. As one of average skill in the art will appreciate, other embodiments may be derived from the teachings of the present invention without deviating from the scope of the claims.

What is claimed is:

1. A method for generating a an oral health care treatment plan for a patient the method comprises the steps of:
 a) providing a list of health care services;
 b) interactively and concurrently selecting a plurality of health care services from the list for proposed treatment of a patient;
 c) inputting digital information regarding the patient;
 d) determining a treatment objective for the patient based on the received digital information;
 e) simulating treatment of the patient using the plurality of health care services based on the received digital information, the treatment objective, and normalized patient data to produce a simulated treatment result; and
 f) generating the oral healthcare treatment plan in accordance with the simulating of the treatment when the simulated treatment results have been acknowledged.

2. The method of claim 1, wherein step (a) further comprises providing a graphic user interface to allow for selection of the list of health care services from a category of well care treatment, emergency treatment, or follow-up treatment.

3. The method of claim 1, wherein the list of health care services includes orthodontic services, dental services, cosmetic services including orthognathic, craniofacial, oral, or plastic surgery services, and medical services.

4. The method of claim 3, wherein the digital information for orthodontics services comprises at least one of: a digital model of the patient's malocclusion, financial constraints, treatment length, desired orthodontic function, desired orthodontic appearance, the patient's dental history, the patient's medical history, and acceptable deviations.

5. The method of claim 4, wherein step (c) further comprises:
 determining whether a sufficient amount of the digital information has been received; and
 when a sufficient amount of the digital information has not been received, prompting for further digital information.

6. The method of claim 4, wherein the normalized patient data comprises orthodontics and other applicable parameters relating to the patient per said selected health care services and wherein step (d) further comprises:
   determining the simulated treatment results per said selected health care services.

7. The method of claim 6 further comprises, depending upon said selected health care services as applicable:
   receiving the dental services from the dental resource;
   receiving the cosmetic surgery services from the cosmetic surgery resource; and
   receiving the medical services from the medical resource.

8. The method of claim 6 further comprises, depending upon said selected health care services as applicable, interacting between: orthodontic resource, dental resource, oral surgery resource, and medical resource to obtain said simulated treatment result.

9. The method of claim 6 further comprises receiving a revised treatment objective in response to the providing an indication that the treatment objectives cannot be obtained.

10. A device for generating a an oral health care treatment plan for a patient the device comprises:
   a processing module; and
   memory operably coupled to the processing module; wherein the memory includes operational instructions that cause the processing module to: (a) provide a list of health care services; (b) prompting a user to interactively and concurrently select a plurality of health care services from the list for proposed treatment of a patient; (c) receiving digital information regarding the patient; (c) determine, either automatically or with user involvement, a treatment objective for the patient based on the received digital information; (d) simulate treatment of the patient using the plurality of selected health care services based on the received digital information, the treatment objective, and normalized patient data to produce a simulated treatment result; and (e) generate the oral health care treatment plan in accordance with the simulating of the treatment when the simulated treatment results have been acknowledged.

11. The device of claim 10, wherein the memory further comprises operational instructions that cause the processing module to provide a graphic user interface to allow for selection of the list of health care services from a category of well care treatment, emergency treatment or follow-up treatment.

12. The device of claim 10, wherein the list of health care services includes orthodontic services, dental services, cosmetic services, and medical services.

13. The device of claim 12, wherein the digital information for orthodontics services comprises at least one of: a digital model of the patient's malocclusion, financial constraints, treatment length, desired orthodontic function, desired orthodontic appearance, the patient's dental history, the patient's medical history, and acceptable deviations.

14. The device of claim 13, wherein the memory further comprises operational instructions that cause the processing module to determine the treatment objective by:
   determining whether a sufficient amount of the digital information has been received; and
   when a sufficient amount of the digital information has not been received, prompting for further disclosure of the digital information.

15. The device of claim 13, wherein the normalized patient data comprises orthodontics and other applicable parameters relating to the patient per said selected health care services and wherein the memory further comprises operational instructions that cause the processing module to simulate the treatment of the patient by:
   determining the simulated treatment results per said selected health care services.

16. The device of claim 15, wherein the memory further comprises operational instructions tat cause the processing module to, depending upon said selected health care services as applicable:
   receive the dental services from the dental resource;
   receive the oral surgery services from the oral surgery resource; and
   receive the medical services from the medical resource.

17. The device of claim 15, wherein the memory further comprises operational instructions that cause the processing module to: depending upon said selected health care services as applicable, to interact between orthodontic resource, dental resource, oral surgery resource, and medical resource to obtain said simulated treatment result.

18. The device of claim 15, wherein the memory further comprises operational instructions that cause the processing module to receive a revised treatment objective in response to the providing an indication that the treatment objectives cannot be obtained.

* * * * *